United States Patent [19]

Solnit et al.

[11] Patent Number: 5,195,952
[45] Date of Patent: Mar. 23, 1993

[54] NOISE REDUCING ASPIRATOR

[76] Inventors: Albert Solnit, 250 N. Robertson Blvd., Suite 401, Beverly Hills, Calif. 90211; Robert Goldstein, 2222 Avenue of the Stars, Suite 805, Los Angles, Calif. 90067; Martin Brouillette, 1649 Ontario, Sherbrooke, (Quebec), Canada, J1J 3T1

[21] Appl. No.: 840,931

[22] Filed: Feb. 25, 1992

[51] Int. Cl.$^5$ .................... A61M 1/00; A61C 17/04
[52] U.S. Cl. ........................... 604/19; 433/91; 604/902
[58] Field of Search ............. 604/21, 19, 45, 119, 604/902; 433/91, 95, 96

[56] References Cited

U.S. PATENT DOCUMENTS

| | | | |
|---|---|---|---|
| 2,711,586 | 6/1955 | Groves | 433/95 |
| 3,516,160 | 6/1970 | Laffler | 433/95 |
| 3,595,234 | 7/1971 | Jackson | 604/119 |
| 3,848,604 | 11/1974 | Sackner | 604/119 |
| 4,049,000 | 9/1977 | Williams | 604/119 |
| 4,204,328 | 5/1980 | Kutner | 433/96 |
| 4,221,220 | 9/1980 | Hansen | 604/119 |
| 4,776,793 | 10/1988 | La Rocca | 433/96 |
| 4,807,625 | 2/1989 | Singleton | 604/95 |
| 4,867,747 | 9/1989 | Yarger | 604/902 |
| 4,878,900 | 11/1989 | Sundt | 604/902 |
| 4,966,584 | 10/1990 | Nguyen | 604/902 |
| 5,013,300 | 5/1991 | Williams | 433/91 |
| 5,024,615 | 6/1991 | Buchel | 604/902 |
| 5,123,890 | 6/1992 | Nates | 433/96 |

Primary Examiner—Paul J. Hirsch
Attorney, Agent, or Firm—Andra M. Vaccaro

[57] ABSTRACT

The present invention is a noise reducing aspirator which is used to carry away air, water, saliva, dental debris from the mouth of a patient or surgical debris. The present invention comprises an open-ended large solid tubular housing having one end adapted to be connected to a source of suction and the other end adapted to be connected to an aspirator tip which will collect air, water, saliva and dental debris. The housing has a sufficient internal ejecting tubular passageway between the ends to accommodate rapid flow of air, water, saliva and dental debris therethrough. The housing includes chamfered pressure venting tubes of equal diameter circularly distributed around, and connecting to, a main suction tube via slanted pathways. The pressure venting tubes reduce and harmonize the noise level of the aspirator and avoid discomforting suction to the patient's tissue. The ends of the housing are designed to secure an aspirator tip or to a source of suction and are designed for easy removal and replacement. The aerodynamic contouring of the present invention ensures that the meeting points of the air flows are as smooth as possible so that shear layer turbulence is reduced to a minimum; resonating cavities, which could create and amplify sound, are eliminated; circular distribution of the pressure venting tubes flatten the intense directional sound peaks originating from the openings of each tube when sound from each tube collides with sound from the others and scatter; and a large solid housing and material selection dampen the minimal amounts of sound produced.

14 Claims, 1 Drawing Sheet

NOISE REDUCING ASPIRATOR

BACKGROUND OF THE INVENTION

1. Field of Invention

The present invention relates to the field of suction devices commonly known as aspirators. Aspirators are used to carry away air, water, saliva and dental debris from the mouth of a patient or to carry away surgical debris from the site of an operation. The present invention is an improvement over existing conventional aspirators primarily due to sound reduction, sound quality improvement and suction efficiency.

2. Description of Prior Art

The most relevant example of prior art is U.S. Pat. No. 3,516,160 filed by Dennis Leffler. Other examples of prior art are U.S. Pat. Nos.: 4,221,220, 3,101,544, 3,101,545, 3,319,628, 4,776,793, and 5,013,300.

The Leffler patent, U.S. Pat. No. 3,516,160, describes a side relief aspirator having two diametrically opposed holes in the sides of a chamber into which a suction tube extends. The disadvantages of the Leffler patent are that air flow from the side holes into the chamber cavity configuration must follow a meanderous path which creates turbulence and therefore sound, and the chamber cavity acts as a pipe resonator which amplifies sound. The present invention is an improvement over the Leffler patent in that the chamber cavity is eliminated and air pressure venting tubes replace the Leffler holes, thereby creating a direct, smoother pathway for air flow. Thus, the device of the present invention reduces turbulence and sound.

U.S. Pat. No. 4,221,220 describes a surgical nozzle and jar to collect surgical debris. The surgical nozzle has air pressure release holes located at the end of the surgical nozzle. A disadvantage of such system is that the release holes generate high levels of sound since there is no barrier between the suction tube and the hole openings. A further disadvantage is that the holes may become clogged with surgical debris since the portion of the nozzle with the holes enter a patient's surgical site. For example, in dentistry, when the holes of the '220 patent become clogged, excessive suction will cause the nozzle to grab the inside of a patient's mouth. The present invention is an improvement over this patent design because pressure venting is accomplished through pressure releasing venting tubes which reduce sound and are located on a portion of the invention which does not enter a patient's mouth.

U.S. Pat. Nos. 3,101,544 and 3,101,545 describe dental saliva ejectors which, unlike the present invention, are incapable of aspirating large dental debris.

U.S. Pat. No. 3,319,628 describes a regulator to control the fluid flow of a suction catheter. It differs in form and function from the present invention which permits a constant flow without the need for varied regulation.

U.S. Pat. No. 4,776,793 describes a funnel shaped attachment to an aspirator which catches excess fluids and debris while preventing splashing. It differs in form and function from the present invention which is designed to suction all fluids and debris and has no opening which excess fluids and debris could exit the aspirator.

U.S. Pat. No. 5,013,300 is an apparatus for lipectomy surgery. It differs in form and function from the present invention which is a relatively simple aspirator device verses the complicated apparatus for lipectomy surgery. U.S. Pat. No. 5,013,300 is a complicated device with sensitive controls for the specific task of removing fatty tissue for cosmetic reasons. The present invention differs in that it is a simple, inexpensive device which aspirates excess fluids and debris.

Generally, the device of the present invention differs from all of the prior art devices due to its aerodynamic contouring. Specifically, the circular distribution of the pressure venting tubes flatten the intense directional sound peaks originating from the openings of each tube when sound from each tube collides with sound from the others and scatter; the large solid housing and material selection of the present invention dampen the minimal amounts of sound produced. Thus, the meeting points of the air flows are as smooth as possible. As a result, shear layer turbulence is reduced to a minimum and resonating cavities, which would create and amplify sound, are eliminated. Further, the device of the present invention also reduces the problem of tissue grabbing, experienced when using many of the prior art devices.

SUMMARY OF THE INVENTION

The present invention relates to a noise reducing aspirator which lowers the sound level and improves the sound characteristics, while maintaining or improving suction performance.

The present invention comprises an open-ended, tubular housing adapted to be held by a dental assistant and having a first end which is connected to a source of suction, which may comprise any convenient suction source normally provided with dental equipment, and a second end adapted to be connected to an aspirator tip for the reception of air, water, saliva and other dental debris. The second end may have a larger interior diameter into which the aspirator tip fits into securely. The larger diameter reduces air friction which may be caused by a joining of the present invention to the aspirator tip by creating a clean flush joint. Both ends are designed for easy removal and replacement of the suction hose and aspirator tip.

The housing also comprises a main portion located between the first and second ends. Air, water, saliva and dental debris will pass from the aspirator tip through the main suction tube running between the main portion and the first and second ends of the present invention to a suction device.

The main housing comprises an air pressure venting means of equal diameter in an angular circular distribution surrounding the second end of the main housing. The venting means are chamfered for a smooth air flow inlet. Each of the venting means connect to the main suction tube via slanted paths having similar diameters and slopes. The existing means permit outside air to gently merge with the air in the main suction tube. The configuration of the venting means release excessive suction and thereby prevent excessive and discomforting suction to the patient's mouth, while reducing noise levels created by prior art devices.

The device of the present invention may include an aspirator tip having an angle fabricated therein for maximum suction of debris. The tip may or may not have holes at the end to be inserted into the patient. Alternatively, the second end of the device may be curved, such that the aspirator tip will be straight.

In use, a patient may be position in a supine position or a semi-reclined position and the present invention is held and usually used by either a dental assistant or patient to periodically clear a patient's mouth of air, water, saliva and dental debris while the patient's mouth is being worked on by a dentist or dental assistant.

OBJECTS OF THE INVENTION

1. Importance of Noise Reduction

During drilling operations, dentists operate in noisy stressful environments. Dentist drills produce loud, audible high-frequency sound. At the same time, prior art aspirators also produce audible high-frequency sound. Repeated exposure to audible high-frequency sound may cause fatigue, stress and loss of hearing. The present invention improves the sound performance of aspirators by reducing the overall sound level both dentists, their assistants and their patients endure during dental work. The noise reduction of the present invention may improve dentists performance by reducing fatigue and stress, thus facilitating an increase in concentration and stamina. The noise reduction of the present invention may most importantly, reduce the potential loss of hearing by the dentist and dental assistants.

2. Suction Efficiency

Dental aspirating suction must also be performed without grabbing the skin inside of the mouth of the patient. To prevent skin grabbing, the present invention has pressure venting tubes through its housing which permit air flow when the aspirator tip becomes plugged. The design of the pressure venting tubes determines the suction efficiency and the magnitude of the grabbing force. Most important, the design of the pressure venting tubes is directly related to the sound output of the aspirator. The present invention is designed to maximize suction performance without grabbing skin and with a minimum output of sound.

DESCRIPTION OF PREFERRED EMBODIMENTS

Figure 1:
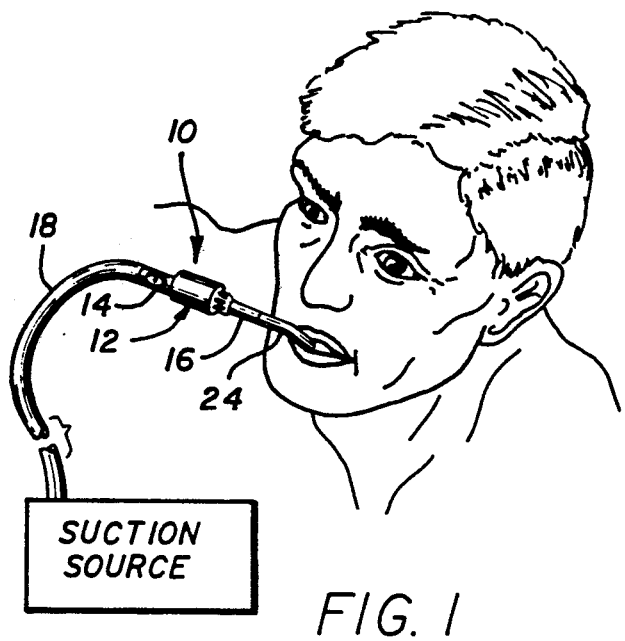
FIG. 1 is a perspective view of the present invention inserted into the mouth of a patient.

Referring to FIGS. 1 through 4, the device 10 of the present invention is shown. The present invention 10 comprises an open-ended, tubular housing 12 adapted to be held by the user (preferably a dental assistant or the patient) and having a first end 14 and a second end 16. The first end 14 has a generally cylindrical shaped configuration adapted to be connected via a conduit 18 to a source of suction (not shown). The suction source may be comprised of any convenient suction source normally provided with dental equipment. In the preferred embodiment, the second end 16 has a collar 22 whereby an aspirator tip 24 for the reception of air, water, saliva and dental or other surgical debris is inserted into end 16 and rests flushly on collar 22. The collar 22 is created by the larger interior diameter of second end 16. The larger diameter reduces air friction which may be caused by joining the device of the present invention 10 to the aspirator tip 24 by creating a clean flush joint. Ends 14 and 16 are designed for easy removal and replacement of the suction conduit and aspirator tip, respectively.

The device 10 defines and provides a main suction passageway 26 extending between the ends 14 and 16 of substantially uniform diameter. Air, water, saliva and dental debris will pass from the aspirator tip 24 through the passageway 26 to the conduit 18 which is connected to a suction device (not shown).

Figure 3:
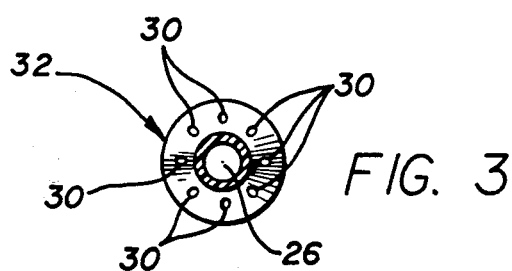
FIG. 3 is a cross-sectional view of the present invention taken along lines 3—3 of FIG. 2.
Figure 4:
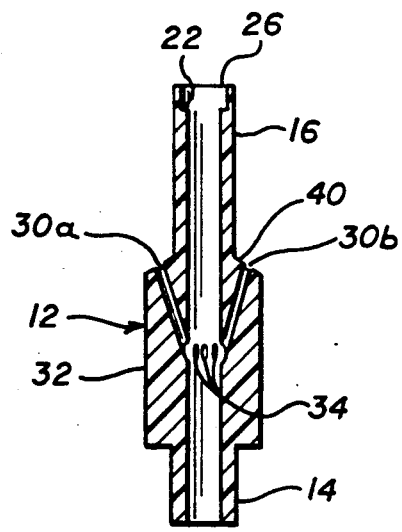
FIG. 4 is a cross-sectional longitudinal side view of the present invention taken along lines 4—4 of FIG. 2.

The device 10 further includes a plurality of pressure venting means 30 which, in the preferred embodiment, are of equal diameter. Referring more particularly to FIGS. 3 and 4, the pressure venting means extend around the circumference of passageway 26, and are located in the main portion 32 of device 10, proximate the second end 16 thereof. The openings shown in FIG. 3 are the ends of pressure venting means 30, two of which are illustrated as 17 and 20. The venting means 30 are chamfered for a smooth air flow inlet. Each of the venting means 30 connect to the main suction passageway openings 34. The venting means 30 permit air flow from the openings 34 to gently merge with the air flowing in the main passageway 26, thereby reducing the amount of noise created by prior art devices. As will be more fully explained below, the venting means further release excessive suction and thereby prevent excessive and discomforting suction to the patient's mouth.

Referring again to FIGS. 1 through 4 in the preferred embodiment, the main portion 32 of device 10 has a first sloped outer surface 40, into which the venting means 30 extend at an angle. In the preferred embodiment, the venting means extend from the outer surface 40 through the main portion 32 of housing 12 into passageway 26 at a 20-45 degree angle.

In the preferred embodiment, the device 10 of the present invention is fabricated out of a plastic material such as Delrin ® acetate or any other material which has good sound dampening properties. Alternatively, the device may be fabricated out of metal, although the amount of sound reduction over the prior art will be sacrificed.

Figure 2:
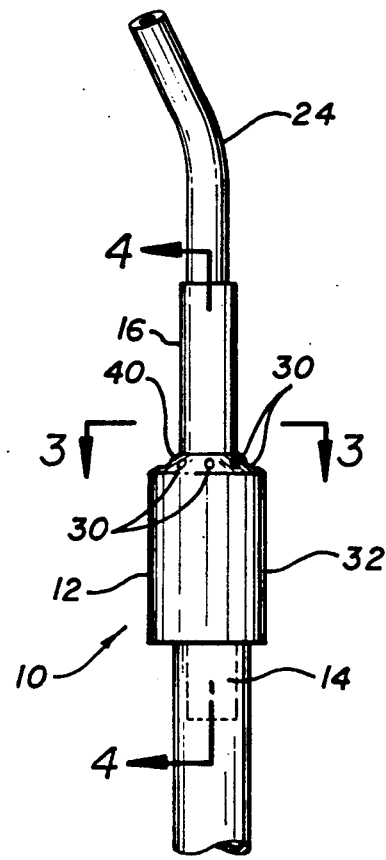
FIG. 2 is a side elevational view of the present invention of FIG. 1.
Figure 5:
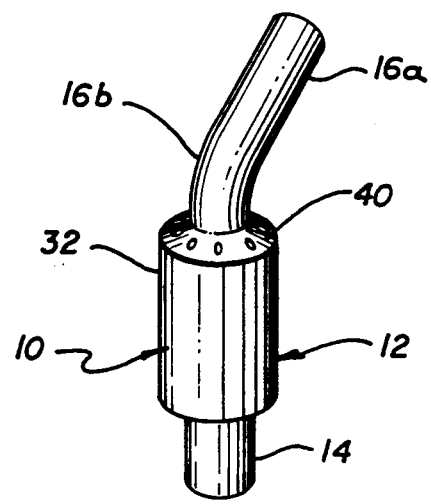
FIG. 5 is a perspective slightly tilted end/side view of an alternative embodiment of the present invention.

As shown in FIG. 2, the aspirator tip 24 is curved at an angle, which, in the preferred embodiment, is approximately 26 degrees. The reason the tip is curved is to allow for easier insertion into the removal site without sacrificing suction or noise reduction. Alternatively, in FIG. 5, an alternate embodiment is shown wherein end 16 of housing 12 having collar 22 is replaced by a curved end 16a, wherein the curve 16b acts to flushly attach the aspirator tip 24 to the housing 12. The bend 16b in end 16a provides the user with an angle by which a straight aspirator tip 24a may be inserted into the patient's mouth.

The device of the present invention reduces the amount of noise output of the prior art devices such as is disclosed in the Leffler patent, U.S. Pat. No. 3,516,160, by 5 to 25 dBs. Specifically, the device of the present invention was tested against existing side relief aspirators (with pressure vents on the aspirator's side) and existing end relief aspirators (with pressure vents on the aspirator's end) in three modes of use: 1) no debris/water flow mode, during which the aspirator is held by a dental assistant but not used for suction; 2) debris/water flow mode, during which the aspirator is used to clean the mouth, 3) plugged mode, during which the aspirator is in use and its tip is held against the inside of the mouth. It is important to distinguish between these modes because the sound resonating during each phase differs.

The test results are as follows: 1) Under the no debris/water flow mode, the present invention reduced sound output by at least 10 dB over the existing side relief aspirators and by at least 2 dB over the existing end relief aspirators; 2) Under the debris/water flow mode, the sound level was reduced by 5 to 10 dB over both existing side and end relief aspirators; 3) under the plugged mode, the sound level was reduced by almost 20 dB over the existing side relief aspirators and 25 dB over the existing end relief aspirators; and 4) the new design of the present invention resulted in lowering and harmonizing the tone of the emitted sound which made the sound more pleasant to hear.

Causation of Sound

Sound output of dental aspirators is caused by air turbulence. The rapid oscillating motions within a turbulent air flow cause the air surrounding the turbulent region to vibrate. This air vibration is perceived to the human ear as sound. Sound output is also generated by the meeting of turbulent air streams flowing at different velocities. This is referred to as "shear layer." Minimizing the meeting point areas and velocity differences between air streams will reduce the sound output. The pressure venting holes of existing conventional aspirators cause meeting points for turbulent air which cause audible high-frequency sound. The configuration of the venting means in the main housing of the present invention minimizes the meeting point areas as well as the velocity differences between the air streams.

The interaction of sound produced by air turbulence travelling through tubes oscillates the frequency of sound and thereby amplifies it. All aspirators have main suction tubes through which air, water, saliva and other debris flow. The tubes oscillate the frequency of the sound and amplify it. The present invention minimizes the main suction tube area, thereby reducing the sound created therein.

The frequency of a sound determines whether it will be perceived by humans as a distracting or disturbing noise, or as a harmonic musical tone. When a sound has a characteristic frequency humans hear a musical tone. When a sound has a random frequency humans hear noise. Tubes change the harmonics of the sound. The length of the tubes determine their resonate frequency. The longer the tube, the lower the sound. The pressure venting means 30 and the main housing 12 of the present invention minimize and harmonize the sound created thereby to create a pleasant tone, thereby reducing noise levels while also minimizing the amount of patient tissue that may be grabbed during the procedure.

Thus, the device of the present invention provides a suction force equal to or better than existing conventional aspirators without grabbing surrounding tissue.

In the preferred embodiment, the venting means comprise eight (8) holes 5/64" in diameter. However, the number of holes and sizes may differ depending on the sound results and suction force required.

In use, a patient may be position in a supine position or a semi-reclined position and the device 10 of the present invention is held and used by either a dental assistant or patient to periodically clear a patient's mouth of air, water, saliva and other debris while the patient's mouth is being worked on by a dentist, dental assistant or surgeon.

While particular embodiments of the invention have been shown and illustrated herein, it will be understood that many changes, substitutions and modifications may be made by those persons skilled in the art. It will be appreciated from the above description of presently preferred embodiments that other configurations are possible and within the scope of the present invention. Thus, the present invention is not intended to be limited to the particular embodiments specifically discussed hereinabove. Although the present invention was designed for use in dentistry, it may also be used in any other field where aspiration is required, such as, but not limited to, surgical lipectomy, general surgery, etc. aspiration is required, such as, but not limited to, surgical lipectomy, general surgery, etc.

What is claimed is:

1. An aspirator for removal of dental, surgical or other debris from a site comprising:
    an open ended, tubular housing having a first end configured to be connected to a source of suction; a second end for reception of surgical or dental debris; a main portion having a larger diameter than said first and second ends, said main portion having an outer surface, a first end proximate said first end of said housing and a second angular end sloping away from said second end of said housing, said tubular housing having a substantially uniform diameter passageway extending from said first end of said housing through said main portion to said second end of housing;
    a plurality of unblocked venting means extending from said outer surface of said second angular end of said main portion through said main portion so as to intersect with said passageway at an angle, said venting means located around said second angular end so as to ensure smoother air flow into said passageway by minimizing the introduction of turbulent air entering the aspirator,
    wherein when said first end of said housing is connected to a suction source, surgical or dental debris will be removed from the surgical or dental site with a minimum of noise and tissue grabbing without the need to block the venting means or stop the air flow into the aspirator.

2. The aspirator of claim 1 wherein said venting means comprise a tubular opening extending from said outer surface of second angular end of said main portion such that it intersects with said passageway at an angle of 20–45 degrees.

3. The aspirator of claim 1 further comprising an aspirating tip means for collecting surgical or dental debris from a surgical or dental site, wherein said tip means is bent at an angle for ease of collection.

4. The aspirator of claim 1 wherein said plurality of venting means comprises 8 holes of 5/64" diameter.

5. The aspirator of claim 1 wherein said second end is bent at an angle for ease of collection.

6. The aspirator of claim 5 further comprising a substantially straight aspirating tip means for collecting surgical and dental debris.

7. The aspirator of claim 1, wherein said venting means are substantially perpendicular to said second angular end of said main portion and shaped to reduce air turbulence.

8. A device for collecting surgical and other debris from a surgical or dental site, comprising:
    an aspirator tip;
    an open ended tubular housing comprising:

a first end;
a second angular end;
first means for removably attaching said first end to a source of suction;
second means for removably attaching said second end to said aspirator tip;
a passageway of substantially uniform diameter extending through said first end of said housing to said second end;
an outer surface;
wherein said second angular end slopes away from said second means,
a plurality of unblocked venting means extending through said housing from said outer surface of said second angular end so as to intersect with said passageway at an angle, said venting means being placed around said second angular end to ensure smoother air flow into said passageway by minimizing the introduction of turbulent air entering the device, wherein when said first means is connected to a suction source and said second means is attached to an aspirator tip, surgical or dental debris will be removed from the surgical or dental site with a minimum of noise and tissue grabbing without the need to block the venting means or stop the air flow into the aspirator.

9. The device of claim 8 wherein said aspirator tip is bent at an angle.

10. The device of claim 8 wherein said second end is bent at an angle for ease of collection.

11. The device of claim 10 further comprising a substantially straight aspirating tip means for collecting surgical and dental debris.

12. The device of claim 8 wherein said second end comprises a collar means for connection with an aspirating tip.

13. The device of claim 8 wherein said venting means comprise a tubular opening extending from said outer surface of second angular end of said housing so as to intersect with said passageway at an angle of 20-45 degrees.

14. The device of claim 8, wherein said venting means are substantially perpendicular to said second angular end of said housing and shaped to reduce air turbulence.

* * * * *